United States Patent [19]

Hanson

[11] Patent Number: 4,823,007

[45] Date of Patent: Apr. 18, 1989

[54] DNA SEQUENCING GEL READING SYSTEM AND METHOD

[75] Inventor: George E. Hanson, Cedar Rapids, Iowa

[73] Assignee: Norand Corporation, Cedar Rapids, Iowa

[21] Appl. No.: 941,684

[22] Filed: Dec. 15, 1986

[51] Int. Cl.[4] .............................................. G01T 1/00
[52] U.S. Cl. .................................. 250/327.2; 250/328
[58] Field of Search ................... 250/327.2, 484.1, 328

[56] References Cited

U.S. PATENT DOCUMENTS 4,110,615 8/1978 McCann ............................. 250/328

FOREIGN PATENT DOCUMENTS 0113678 7/1984 European Pat. Off. ......... 250/327.2

Primary Examiner—Carolyn E. Fields
Assistant Examiner—Richard Hanig
Attorney, Agent, or Firm—Neuman, Williams, Anderson & Olson

[57] ABSTRACT

In place of the conventional photographic DNA sequencing gel method, the present disclosure proposes directly scanning the radio labeled DNA fragments of successive information tracks on the gel to produce an on-line contemporaneous display. In this way, the scanning and/or display may be modified during the progress of the scanning operation, for example to emphasize the development of selected portions of the gel which exhibit relatively faint radioactivity. The scanning operation preferably takes place by a constant speed rotation of the gel and an arcuate scanning of a radioactive detector head with the schedule of angular velocity of the detector varying to maintain a relatively constant relative scanning velocity between the detector head and successive points on the surface of the gel. The direct electronic storage of the gel track configuration results in a facilitation of the reading of the gel in comparison with the laborious procedure required for visually reading the DNA sequence from a photograph of the gel.

20 Claims, 2 Drawing Sheets

U.S. Patent   Apr. 18, 1989   Sheet 1 of 2   4,823,007
FIG. 1
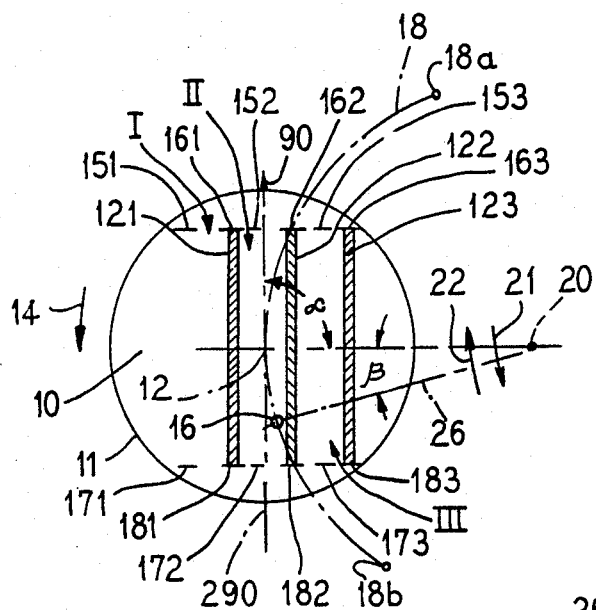
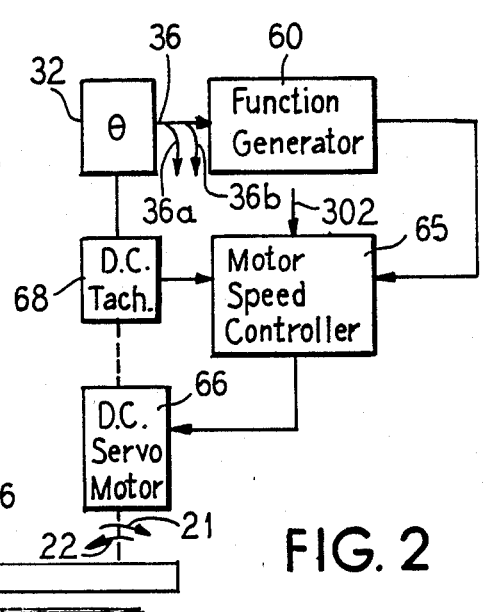
FIG. 2
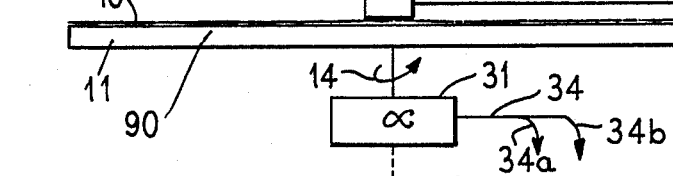
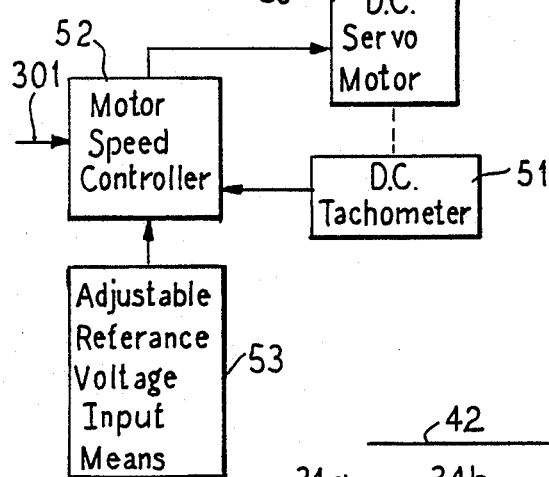
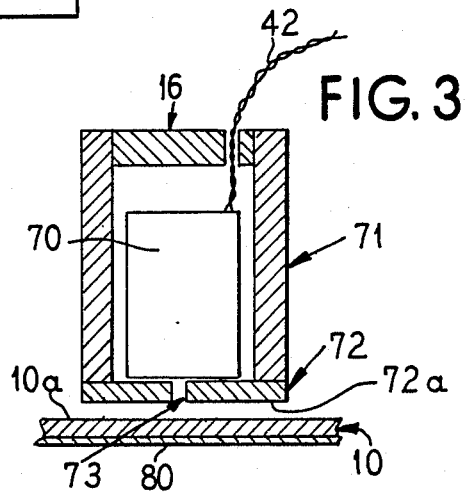
FIG. 3
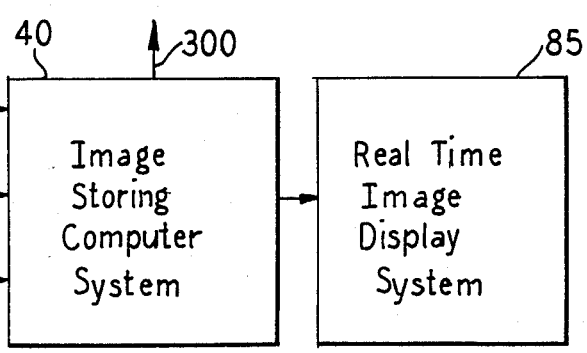
FIG. 4

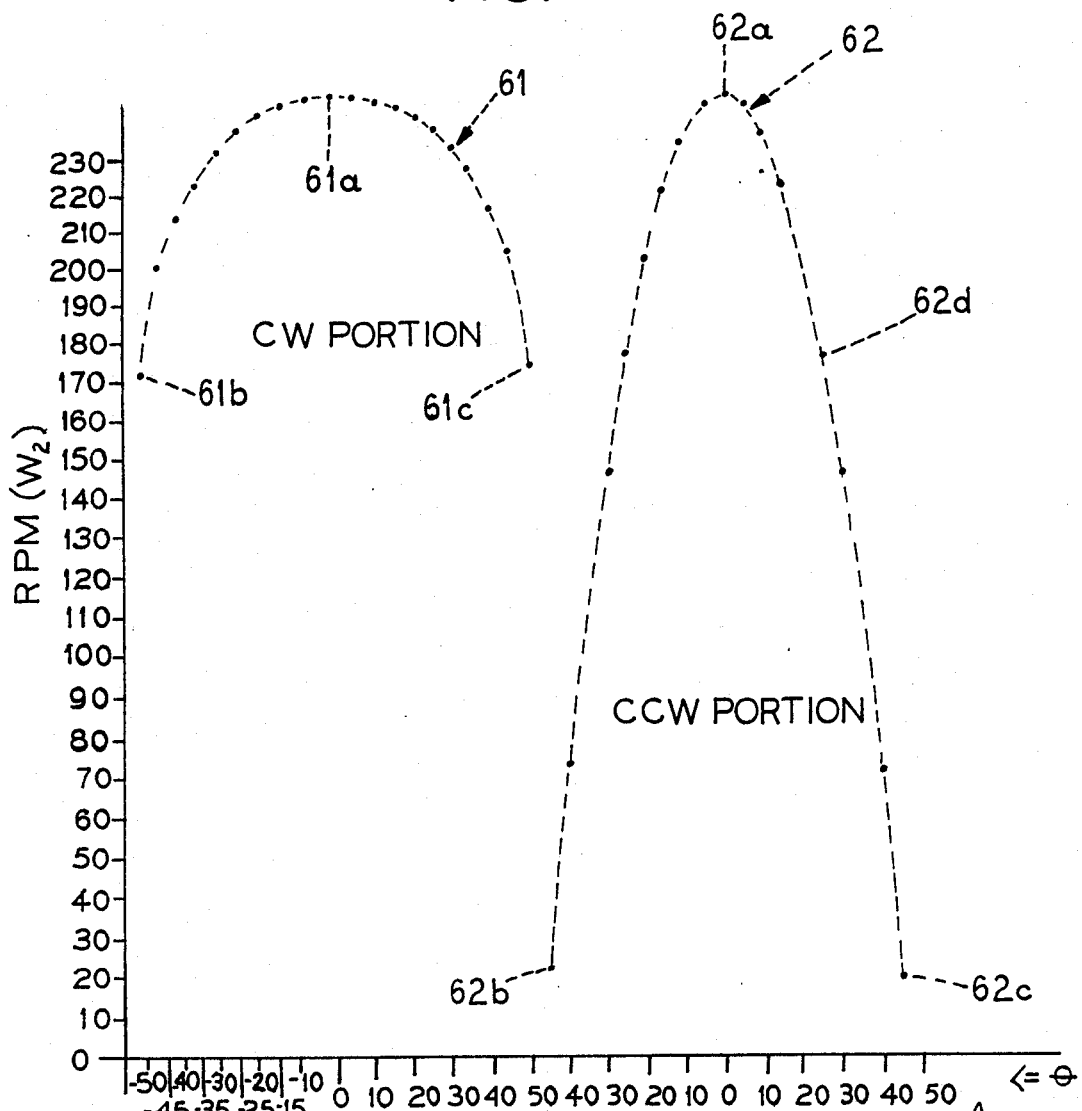
FIG. 5
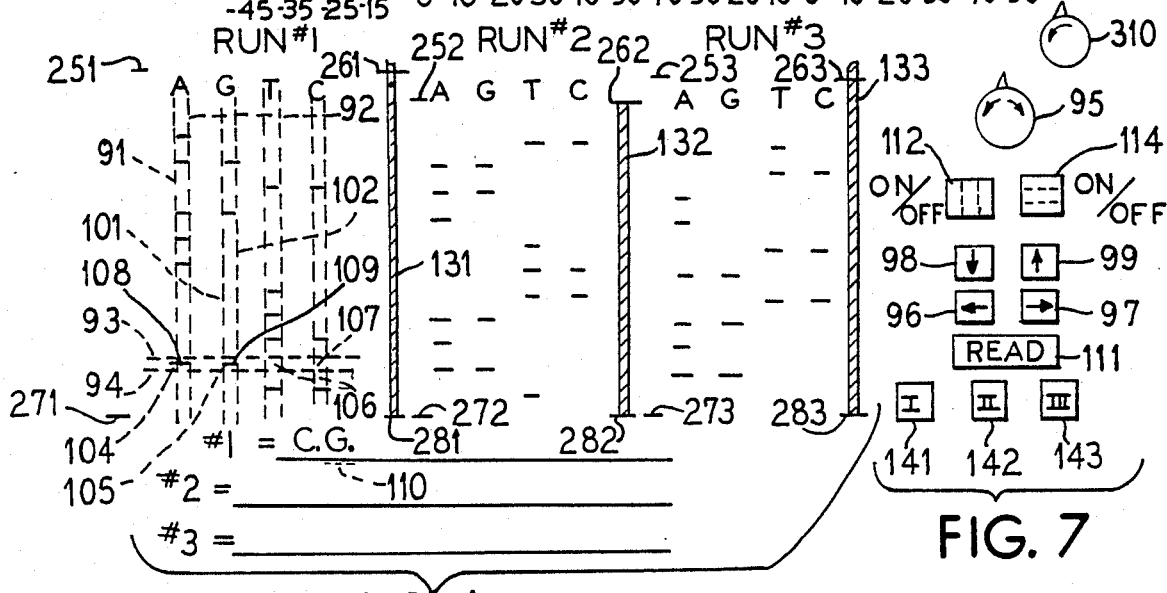
FIG. 6
FIG. 7

DNA SEQUENCING GEL READING SYSTEM AND METHOD

BACKGROUND OF THE INVENTION

This invention relates to a system and method for the reading of electrophoresis gels containing radiolabeled genetic material.

In the field of genetic engineering, it has been a common procedure to produce a photographic or x-ray film auto-radiographic image of DNA sequencing gels and then to laboriously read off the sequences of bases from visual inspection of the film. Such a visual analysis of an auto-radiogram is extremely time consuming and prone to many errors. Furthermore, the exposure time for an auto-radiogram is usually selected based on approximations and rules of thumb, so that the production of such auto-radiograms itself presents difficulties. Where an intensifier plate is utilized with the film to enhance the image intensity, the sharpness of the image is inherently reduced.

Accordingly, it would be highly advantageous if the step of preparing an auto-radiogram film image could be omitted and if the DNA sequence information could be read directly from the gel itself. It would also be advantageous if the information from the gel could be read directly into a computer image storage system, and if the development of the computer image could be observed and selectively controlled.

SUMMARY OF THE INVENTION

It is an object of the present invention to provide a system and method for generating a computerized record of the radiation pattern associated with a sequencing gel, thereby to avoid the need for the production of a film image of the radiation pattern.

Another object is to provide a sequencing gel imaging system and method wherein an image can be observed essentially in real time during its generation, such that selected segments of the gel can receive more intensive scanning where needed for an optimal sequencing analysis.

A feature of the invention resides in the provision of a DNA sequencing gel reading system wherein the radiation field of the gel itself is scanned while the gel is rotated continuously.

A further feature resides in the provision of an automatically operating, sequencing gel scanning system having provision for manual override to effect more intensive scanning at selected segments of the gel.

Other objects, features and advantages of the invention will be apparent from the following detailed disclosure taken in connection with the accompanying drawings and from the individual features and relationships of the appended claims.

BRIEF DESCRIPTION OF THE DRAWINGS

FIG. 1 is a diagrammatic illustration useful for explaining the operation of a sequencing gel scanning system and method in accordance with a preferred embodiment of the present invention;

FIG. 2 shows a specific implementation of a preferred embodiment of the present invention;

FIG. 3 shows an exemplary detector head for the embodiment of FIG. 2;

FIG. 4 is a block diagram for illustrating further components of a preferred embodiment, which may also include the components of FIGS. 2 and 3, for example;

FIG. 5 is a graphical view for showing an exemplary variation of angular velocity of the detector of FIGS. 1, 2 and 3, in a preferred system and method according to FIGS. 1-4;

FIG. 6 illustrates diagrammatically a portion of the display screen of the real time image display system of FIG. 4; and FIG. 7 indicates controls for the display illustrated in FIG. 6.

DETAILED DESCRIPTION

In the illustrated embodiment, a DNA sequencing gel as indicated at 10, FIG. 2, is disposed on a rotatable support 11 which is mounted for rotation about a central vertical axis 12. Typically, such gels are radioactively tagged with a phosphorus isdotope ($P^{32}$). In the system of FIG. 1, support 11 may be rotated continuously at constant speed in the direction of arrow 14, and a radiation detector indicated at 16 is cyclically scanned along a path such as indicated at 18 which may traverse the gel surface between respective end points 18a and 18b which lie generally oppositely offset from the rotatable support.

In a preferred scanning pattern, the detector 16 is moved along an arcuate path as shown at 18, FIG. 1, by rotating the detector about a rotational axis 20 and moving the detector 16 alternately in a counterclockwise direction as indicated by arrow 21 and in a clockwise direction as indicated by arrow 22. Where an angle theta ($\theta$) is measured between a line 24 connecting axis 20 with axis 12 and the longitudinal axis of a mounting arm 26 carrying the detector, the arm 26 may scan cyclically over the support 11 between a position theta equals plus fifty degrees and a position theta equals minus fifty degrees, and may reverse direction at respective end positions 18a and 18b each about two inches from the edge of support 11. The angular velocity of the mounting arm 26 may be varied as a function of the angle theta such that the magnitude of the resultant velocity of detector 16 relative to the gel 10 is essentially constant in the active scanning region. The resultant scanning pattern of detector 16 over the gel 10 preferably essentially uniformly covers the entire surface area with a resolution at least comparable to the resolution provided by the use of a photographic film. By way of example, the reading of the radiation field of the gel 10 may be recorded by triggering a processor interrupt for each radiation particle sensed by detector 16 and by recording the number of interrupts for each element of the gel surface, on a non-volatile medium such as a hard data storage disk during the scanning process. Each segment of the stored image can be displayed on essentially a real time basis and the scanning can be continued until an optimum image has been developed for each segment. The display segments may have a horizontal or vertical axis corresponding to the direction of the sequences of successive bases to be analyzed.

In the embodiment of FIG. 2, the angular position of support 11 is sensed by a shaft angle encoder 31, and the angular position of mounting arm 26 is registered by means of a shaft angle encoder 32. The encoder position signals may be supplied via output lines such as 34, 34a and 35, and 36, 36a and 37 to a computer system 40, FIG. 4, which may define a matrix of elemental scanning regions over the surface of support 11, based on the encoder signals supplied thereto at 35 and 37. A further input 42 to computer system 40 may supply each particle detection pulse from detector 16 as an interrupt signal. A count of such interrupt signals for each elemental scanning region may be transferred to a nonvolatile memory of system 40, for example, a hard data storage disk.

In the example of FIG. 2, a suitable constant speed drive for support 11 may comprise a DC servo motor 50 which drives support 11, encoder 31 and a DC tachometer 51. The DC output of tachometer 51 may be supplied to a controller 52 having an adjustable reference voltage. A comparator circuit, e.g., type CA 3160, of component 52 may adjust the speed of servo motor 50 until the output of tachometer 51 corresponds with a selected reference voltage, and thereafter essentially maintain the speed at a selected value. As indicated in FIG. 2, the value of reference voltage may be manually selected by means of an adjustable input device 53, e.g., a potentiometer or a digital input selector associated with a digital to analog converter, having a manual control coupled therewith as indicated at 54.

For the case where detector mounting arm 26 is to be driven at variable speed, a function generator 60 may receive the encoder signal from encoder 32 and supply a respective voltage value for each encoded position representing the desired speed. FIG. 5 shows an example of desired angular velocity of mounting arm 26 as a function of angular position theta. As is understood in the art, function generator 60 may comprise a solid state memory device wherein the encoder signal at 36 serves to generate successive digitally coded addresses, the respective stored function values at the successive addresses corresponding to curves 61, 62, FIG. 5. The digital function values read out from the memory device of component 60 may be converted to proportionate analog voltages by a digital to analog converter, such analog voltages being supplied to controller 65 as reference voltages. The controller 65 then serves to maintain the speed of operation of servo motor 66 for successive encoder values such that the output of DC tachometer 68 essentially corresponds with the successive reference voltage values from function generator 60. With proper selection of the stored function values in component 60, and a given rotational rate of support 11, the resultant velocity of detector 16 relative to the surface of gel 10 may be maintained essentially constant as the detector 16 moves along the path 18. Generally, as indicated by curves 61 and 62 in FIG. 5, the angular velocity of arm 26 may have a maximum value (e.g. at 61a, 62a FIG. 5) as the detector 16 crosses the central axis 12 (theta equals zero) and may have relatively minimum values as the detector scans at the periphery of the support 11 where the support has maximum tangential velocity.

Where the path 18 is arcuate as shown, the tangential velocities of the elemental scanning regions of the gel 10, and of the detector 16, have additive components as the detector moves from end point 18a to end point 18b, and have opposing components as the detector moves from point 18b to point 18a. The curve 61 of FIG. 5 representing movement from end point 18b to end point 18a thus differs from curve 62 representing movement from end point 18a to end point 18b.

FIG. 3 indicates a preferred detector configuration, wherein a Geiger-Mueller tube 70 is provided with a shielding housing 71 and with a collimator plate 72 having a collimating orifice 73 of cross section and depth to provide the desired resolution, for a given required clearance between the collimator face 72a and surface 10a of the gel 10.

After electrophoresis, the gel medium is suctioned through a filter paper base which then serves as a backing as indicated at 80 in FIG. 3. The composite formed by gel layer 10 and backing layer 80 resembles ordinary black and white photographic material in its stability and can be spun on support 11 at a high rotational rate, e.g., three hundred revolutions per minute. Where the support 11 has a radius of twelve inches, the arm 26 may provide a radius arm of e.g. sixteen inches. Curves 61 and 62 may then represent maximum angular rates at 61a and 62a (i.e. at theta equals zero angular degrees) of 238.7 revolutions per minute for example, and may represent angular rates at 61b and 61c of 171.8 revolutions per minute, and angular rates at 62b and 62c of about 21.6 revolutions per minute (these points corresponding to values of theta of plus or minus fifty angular degrees).

By way of specific exemplary details, encoders 31 and 32 may supply a pulse for each increment of rotational movement at respective conductors 34a 36a and may supply a marker pulse to a respective conductor 34b 36b at a selected unique angular position representing an encoder zero count position. For example, at the zero count position of encoder 31, the gel 10 on support 11 may have a given orientation corresponding to a vertical display orientation on display system 85, FIG. 4. Thus, with the direction of the sequencing gel tracks on the layer 10 parallel to a line through central axis 12 and through a mark 90 on the periphery of the support 11, the radiation images of such gel tracks will always be disposed parallel to the vertical axis on the display of system 85. The zero count position of encoder 32, on the other hand, may correspond with an end position of path 18 such as 18a.

FIG. 6 illustrates diagrammatically a portion of the display screen of real time image display system 85, FIG. 4. During the development of the image of FIG. 6 with the progressive scanning of the sequencing gel 10, a set of tracks labeled as run #1 which are the result of a first application of DNA samples, for example, may appear as fainter than later applied runs such as labeled #2 and #3. By applying the successive runs in precisely defined channels on the gel, it is possible to cause the computer system 40 during further scanning of the gel 10, to only store radiation signals detected from the first channel region of the gel 10. Thus the readings for run #1 may be darkened, without over-exposure of the display for runs #2 and #3, for example.

When each run has been displayed with optimum clarity, for example by selective electronic storage of radiation signals from one or more of the runs during a second phase of the scanning operation, the completed display may include a portion such as shown diagrammatically in FIG. 6.

If desired, the time of application of each sample, and the power utilized may be stored with the scanning results for each run, so as to be displayed with the run number. Other pertinent information may also be stored for each run so as to be displayed by the image display system 85, e.g. as part of a heading for the respective sets of lanes as shown in FIG. 6.

The actual reading of the gel sequence may be mechanized. For example as shown in FIG. 6 for run #1, reference column lines such as 91 and 92 may be generated for defining each track such as the "A" track for run #1 in FIG. 6. Corresponding locations of the respective tracks such as the "A", "G", "T" and "C" tracks of run #1 may also be defined by reference lines such as 93 and 94. By way of example, the display may be adjusted angularly e.g. by means of a control knob 95, FIG. 7, so that run #1 is essentially vertically disposed on the display, the reference lines such as 91, 92 being generated as vertical lines, and the reference lines such as 93, 94 being generated as horizontal lines on the display. The separation of lines such as 91 and 92, and such as 93 and 94 may be selected by entering corresponding numerical parameters e.g. via a conventional personal computer keyboard. The pairs of reference lines such as 91 and 92 may be moved horizontally as a group of four such pairs by means of a suitable manually operated control, such as indicated at 96, 97, and the pairs of reference lines such as 93, 94 may be moved vertically by a similar manual control 98, 99 as successive bases of a sample are read. The space between successive pairs of vertical reference lines such a 91, 92 and 101, 102 may be adjusted by designating the respective sets as "A", "G", "T", or "C", and then selecting one of the sets e.g. via the keyboard and then operating the horizontal control 96, 97. Automatic circuits of computer system 40 may then examine the memory locations defined by windows 104–107 which are framed by the intersecting pairs of lines, e.g. 91, 92 and 93, 94, and automatically determine the presence of radiation regions such as 108, 109 at windows such as 104 and 105. Thus for the second row of run #1, being defined by reference lines 93, 94 in FIG. 6, the computer system could automatically determine the presence of the "G" base, and print out the result at the location of cursor 110. For example a read control key 111 may be actuated to signal when the windows are to be read by the computer system 40. The four pairs of reference lines such as 91, 92, 101, 102, may be turned on and off by a control 112. The length of lines 93, 94 and their separation may be selected via the keyboard. An on-off control for the horizontal pair of reference lines 93, 94 is indicated at 114.

As indicated at 121–123 in FIG. 1, at the time of application of each run, a reference lane may be provided having a tracer material or marker substance which can be optically or radioactively scanned to assist in identifying the locations of the successive runs. Such lanes may be visually observed so as to facilitate positioning of the gel 10 relative to marker 90 on the support 11.

By first scanning the reference lanes such as 121–123 on the gel 10, e.g. with the radiation scanner 16 sensitive to the radiation from the tracer material, a set of corresponding dark solid reference lines such as 131–133, FIG. 6, can be first generated on the display and used to define the positions of zones such as I, II, III, etc. on the gel 10 where the runs #1, #2, #3, etc. to be scanned, are located. An optical scanner may be interchangeable with radiation scanner 16 so as to trace exactly the same scanning raster on gel 10 as scanner 16, where the reference lanes 121–123 are not radioactive. As another example, an optical scanner may be insertable into collimating orifice 73, FIG. 3.

The computer system 40 may be addressed according to the successive readings of encoders 31 and 32, and a maximum intensity value may be stored for each memory location corresponding to scanning of reference lanes 121–123.

Where the display system 85 utilizes a display with a conventional line-by-line rectilinear display raster, the originally received encoder address for each point of the lanes 121–123 may be converted to a rectilinear coordinate system such that each corresponding marker line such as 131–133, FIG. 6, on the display will be vertical. Then zones I, II and III in FIG. 1 will each lie between fixed horizontal address values with respect to the rectilinear coordinate system. Accordingly, during a radiation scanning operation, the computer system 40 may convert each new encoder address to a corresponding rectilinear display address, and determine the zone number (e.g. I, II or III) for such encoder address while the region of gel 10 with such encoder address is being scanned. The radiation signal pulses from scanner 16 for each display address may be counted in an accumulator and stored in the rectilinear display memory in real time.

If after an initial phase of the radiation scanning operation, the operator decided that zones II and III were properly developed, but the operator desired further scanning of zone I only, the operator could depress zone-complete buttons such as 142 and 143, FIG. 7, to terminate the recording of radiation counts for zones II and III, FIG. 1, while leaving zone I button 141 unactivated so as to continue to store radiation counts for each encoder address falling within zone I. Each zone could be further subdivided e.g. into three vertical segments, so that different portions of any of the zones could be differently developed simply e.g. by pressing respective ones of nine zone segment-complete buttons at respective different times during the radiation scanning process.

In order to further define zones I, II and III, radioactive marks 151, 161 and 171, 181 may be deposited at the beginning and end of the application of DNA run #1, marks 152, 162 and 172, 182 may be deposited at the beginning and end of run #2, and marks 153, 163 and 173, 183 may be applied at the beginning and end of the application of run #3. This provides convenient reference points such as shown at distinctive transverse line marks 251–253, 261–263, 271–273 and 281–283, FIG. 6, for delineating common points along the runs, and for establishing the transverse direction for purposes of the reading the corresponding rows of the A, G, T and C tracks. This can be true even where the radioactive tracer materials of reference lanes 121–123 are scanned by radioactive scanner 16.

Where the tracks are each straight lines and parallel on the gel 10, the horizontal reference lines 93, 94 will line up with marks such as 271, 281 at the beginning of reading of a run, and will line up with makes such as 251, 261 at the end of a run. Of course, intermediate marks between marks such as 151 and 171, 161 and 181, etc. may be deposited during the application of each run to the gel to provide any desired number of reference marks between marks such as 251 and 271, 261 and 281, etc., on the display.

The continuous lines 131–133, FIG. 6, are preferably produced by delivering a continuous stream of radioactive tracer material at the starting point for each run, e.g. via a micropipette operating in step with the application of the DNA samples.

Where, as is not uncommon, the tracks of a run curve somewhat, the curvature will also appear at the reference tracks 121–123 and in the relationship of the deposited reference mark pairs such as 151, 161 in relation to a vertical gel axis such as 290, FIG. 1.

If desired, the initial contents of the display memory may be stored on a hard disk storage unit or the like as a permanent record, and then the data may be processed to produce vertical tracks. For example, by use of a suitable keyboard code, the angle of lines 93, 94 may be controlled via knob 95 to define the angle of each set of reference marks such as 251, 261 and 271, 281, whereupon the computer system 40 may interpolate the degree of curvature for each successive A, G, T, C row for each track, and redefine the addresses for each pixel of the display so that the tracks are all vertical with the corresponding A, G, T, C values of each row being displayed in horizontal alignment. Suitable linear recession routines for carrying out such transformations are well known in the art. If the transformation is accurate, displayed reference lines will become straight and vertical, and reference marks such as 251, 271 will be in precise vertical alignment.

Where reference lanes 121-123 and transverse line marks 151-153, 161-163, 171-173 and 181-183 are all produced by radioactive tracer materials and are scanned radioactively by scanner 16, the selectors 141-143 may be programmed by the keyboard to terminate storage of readings for these indicia early in the scanning process when the corresponding lines 131-133 and transverse marks 251-253, 261-263, etc. have optimum clarity and sharpness. At this time, zones I, II, III, etc. may be quantitatively defined, and selectors 141-143 programmed via the keyboard so that a further actuation thereof will terminate storage of values for respective lanes or runs or segments of respective zones as previously described. Of course, the content of the display memory may be recorded at different points during the scanning process, e.g. on a hard disk unit, so that recording of scanning values could be resumed from such recorded phases in the scanning process if desired.

SUMMARY OF OPERATION

In operation of a system such as indicated in FIGS. 1-7, a DNA sequencing gel 10 on a suitable backing is trimmed so as to fit on a turntable 11. The turntable may have a surface with a diameter of twenty-four inches, for example. As indicated in FIG. 1, the gel 10 may have marker tracks 121-123 formed by a marker substance which may be optically visible so as to facilitate placing the gel on the turntable with the information tracks parallel to a reference line indicated at 290 which joins the central axis 12 of the turntable with a marker 90 at the periphery of the turntable.

In the illustrated embodiment of FIG. 2, a detector 16 sensitive to the labeling of the DNA fragments and sensitive to the labeling of the substances forming the marker tracks 121-123, is mounted on an arm 26 and rotated about an axis 20 so as to reciprocally scan along a scanning path indicated at 18 between end points 18a and 18b.

As represented in FIG. 5, during movement of the arm 26 from point 18a to point 18b, the angular velocity of the arm 26 varies, beginning at a relatively low velocity as indicated at 62b, having a progressively increasing velocity up to a maximum angular velocity at point 62a, and then having a progressively reducing velocity including a velocity as indicated at 62d for the particular angle alpha shown in FIG. 1 (with motion in the counterclockwise direction as indicated by arrow 21, FIG. 1), and reaching a minimum angular velocity as indicated at 62c as the detector 16 moves beyond the lower perimeter of the turntable 11. In the return direction of motion from point 18b to 18a, the velocity varies as indicated for curve 61, FIG. 5, with the detector 16 having a relatively high velocity as indicated at point 61b as it crosses the lower periphery of the turntable 11, the angular velocity progressively increasing until a velocity as indicated at 61a is atained as the detector 16 crosses the central axis 12 moving in the direction of arrow 22, then FIG. 1. The velocity then progressively decreases so that the velocity is as represented at 61c in FIG. 5 as the detector 16 moves across the upper periphery of the turntable 11.

Encoders 31 and 32, FIG. 2, define the instantaneous angular positions of turntable 11 and detector 16 so as to define the addresses at which the respective scanning values from detector 16 are to be stored in the computer system 40. As previously explained, for the case of the particular scanning geometry of FIG. 1, and for the case of a rectangular display raster of system 85 as indicated in FIG. 6, the instantaneous addresses from encoders 31 and 32 may be converted instantaneously to rectangular coordinates by the computer system 40, and the scanning values may then be stored in a system 40 with such rectangular computed addresses. Thus, as scanning progresses as indicated in FIG. 1, the information tracks of regions such as indicated at I, II, III in FIG. 1 may be displayed as they are being developed as indicated in FIG. 6. The marker tracks 121-123 and the information tracks may be similarly radioactively labeled, and detector 16 may be a radioactive detector, so that the information tracks and marker tracks are all simultaneously scanned by the detector 16, and the results of each scanning movement of the detector 16 are contemporaneously displayed on the display system 85.

At the time of depositing the DNA fragments of each set of tracks for electrophoretic development, marker substances may be intermittently deposited for example at frequent intervals as indicated at 151, 161 for the information tracks of region I, FIG. 1, and as indicated at 171, 181, FIG. 1, for example, so that these marker means 151-153, 161-163, 171-173 and 181-183, etc., may be scanned simultaneously with the scanning of the information tracks and the marker tracks 121-123. By way of example, marker such as 151-161 may be located at one-inch intervals along the respective sets of information tracks, so that corresponding markers such as indicated at 251-253, 261-263, 271-273 and 281-283, FIG. 6, will appear on the display on the component 85 essentially at corresponding one-inch intervals.

As previously described, if during development a particular segment of the display of component 85 has completed its development prior to the other segments, a corresponding zone complete button such as indicated at 141-143, FIG. 7, may be actuated to discontinue storage of signals from the detector 16 with addresses aligned in the corresponding zone. For example, if the display for zone I reaches completion, the zone complete actuator 141 may be manually depressed to discontinue storage of scanning values at addresses corresponding to zone I, FIG. 1. Of course, the computer system 40 may include a suitable mass storage means such as a hard storage disk which continues to store signals from the detector 16 for all zones throughout a scanning operation, in addition to the storage of the scanning values in the image display system associated with the real time image display system 85. Furthermore, as represented by output 300 of computer system 40, and by control inputs 301 and 302, FIG. 2 to motor speed controller components 52 and 65, the computer system can modify the scanning operation in desired preprogrammed manners in response to manual selections via a keyboard based on operator decisions as the operator views the display of FIG. 6 during the progress of the scanning operation. For example, the detector 16 could be moved more slowly so as to develop higher radiation counts for successive scanned points at the periphery of the gel 10 during a further phase in the scanning operation. Furthermore, the real time image display system 85 may have a zoom function so that such a peripheral portion of the gel could be displayed on a larger scale during the scanning operation, or thereafter during the gel reading process, FIG. 7 including a zoom control 310 for this purpose.

A previously described, reference lines, such as 91,92 and 93,94 may be manipulated relative to the displayed sets of information tracks by means of angular adjustment control 95, horizontal adjustment controls 96,97, vertical adjustment controls 97,98 and on/off controls 112,114, all in conjunction with a typical personal computer keyboard, as previously described.

It will be understood by those skilled in the art that the image display system 85 may be readily provided with controls such as indicated in FIG. 7, so as to generate the reference means such as 91-94, FIG. 6. Also, the computer system 40 is readily constructed so as to respond to controls such as 111 and 141-143 so as to automatically read the density of display in window regions such as indicated at 104-107, FIG. 6, and so on as here described.

Thus, the system of FIGS. 2 and 4 adequately depicts for those skilled in the art the means for displaying the reference lines such as 91-94 and the control means for positioning reference lines such as 93,94 relative to information marks such as indicated at 108,109, FIG. 6, so as to identify respective corresponding points on the respective information tracks of a set such as the set in region I, FIG. 1. It will be understood that the image display system 85 may contain any conventional electronic image display means such as a cathode ray tube with extremely high resolution comparable to that provided by the conventional photographic gel reading system.

It will be apparent that many modifications and variations may be effected without departing from the scope of the novel concepts and teaching of the present invention.

I claim as my invention:

1. In a system for the reading of a gel containing labeled material which has been distributed by electrophoresis,
    rotatable support means for mounting a gel for rotation about an axis of rotation,
    detector means sensitive to the labeled material,
    scanner mounting means mounting the detector means for scanning movement across the rotatable support means for scanning along successive paths on a gel during rotation thereof, for scanning the gel surface,
    encoder means coupled with the rotatable support means and with the scanner means for encoding each scanning position of the detector means, and
    signal storage means coupled with the detector means and with the encoder means for storing the output of the detector means as a function of scanning position.

2. In a system according to claim 1, drive means coupled with said rotatable support means and with said scanner mounting means for maintaining a generally constant relative scanning velocity between said detector means and a surface of a gel mounted on said rotatable support means.

3. In a system according to claim 1, said scanner mounting means comprising a mounting arm rotatable about an axis offset from the axis of rotation of the rotatable support means by a distance at least comparable to a radial dimension of the rotatable support means.

4. In a system according to claim 3, said scanner mounting means mounting, the detector means for scanning along an arcuate path essentially crossing the axis of rotation of the rotatable support means.

5. In a system according to claim 4, drive means producing rotation of said rotatable support means essentially at a constant speed, and moving said detector means at a relatively low speed at a peripheral region of the rotatable support means and at a progressively higher speed as the detector means approaches the axis of rotation of the rotatable support means.

6. In a system according to claim 1, a gel on said rotatable support means having respective marker tracks developed thereon by electrophoresis and being scanned by said detector means to transmit to said signal storage means the location of respective zones which can thereafter be preferentially scanned.

7. In a system according to claim 1, a gel on said rotatable support means having respective sets of marker substances thereon distributed by electrophoresis in a direction of migration so as to define transverse reference lines transverse to such direction of migration.

8. In a system according to claim 7, said detector means scanning said marker substances so as to produce stored marker signals in said signal storage means, and display means coupled with said signal storage means for displaying visual markers in accordance with the location of corresponding respective marker substances on said gel.

9. In a system according to claim 8, said gel having respective marker tracks defined by marker material capable of being scanned and having been distributed along lines on the gel by the action of electrophoresis, said detector means scanning said marker material to effect storage of maker signals in said signal storage means, and said display means displaying marker lines corresponding to the respective marker tracks along with a display corresponding to the distribution on the gel of the labeled material which has been distributed by electrophoresis.

10. In a system according to claim 1, a gel having respective sets of information tracks including labeled material distributed thereon by electrophoresis,
    detector means sensitive to the labeled material scanning a surface of the gel to produce information signals in accordance with the distribution of the labeled material of the information tracks on the gel, and
    on-line display means coupled with the detector means for displaying the distribution of the labeled material of the information tracks during the scanning thereof by said detector means.

11. In a system according to claim 10,
    means operable during a scanning operation for selectively emphasizing respective different segments of the displayed image and for storing further scanning values from the detector means for selected segments being emphasized, during further scanning by the detector means.

12. In a system according to claim 10,
said gel having labeled marker tracks extending parallel to the information tracks,
said display means displaying the location of the marker tracks along with the information tracks during a scanning operation.

13. In a system according to claim 10,
said gel having labeled marker means distributed thereon by electrophoresis contemporaneously with the labeled material of the information tracks, and
said display means displaying the location of the labeled marker means during the scanning of the gel by the detector means.

14. In a system according to claim 10,
said gel having labeled DNA fragments distributed along the information tracks of each set by electrophoresis for identifying respective bases of the DNA, and
said gel having labeled marker means deposited intermittently during electrophoresis, and
said display means displaying the location of the labeled marker means and the distribution of the labeled DNA fragments during scanning of the gel by said detector means.

15. In a system according to claim 14, said labeled marker means being deposited at opposite lateral sides of each set of information tracks for defining a transverse direction, thereby to delineate corresponding portions of the respective information tracks of each set.

16. In a system according to claim 15, means for displaying horizontal reference lines on the display means, and means for displaying the labeled marker means associated with a set of information tracks so as to be essentially aligned in a horizontal direction.

17. In a system according to claim 10, means for displaying vertical reference lines on the display means and for displaying the sets of information tracks so as to extend generally parallel to the vertical reference lines on the display means.

18. In a system according to claim 10, means for displaying horizontal reference lines on the display means, and control means for positioning the horizontal reference lines so as to identify respective corresponding points on the respective information tracks of a set.

19. In a method of reading a DNA sequencing gel having a set of information tracks defined by labeled DNA fragments distributed by electrophoresis, said method comprising
directly scanning the gel by positioning the gel in a plane and rotating the gel about an axis of rotation transverse to said plane while moving a detector sensitive to the labeled DNA fragments in a path which is adjacent to said plane of the gel and transverse to said axis of rotation, and
optically displaying the results of the scanning operation on an electronic display screen.

20. In a method according to claim 19, the optically displaying step taking place at an intermediate stage in the scanning operation such that further scanning of the gel can be utilized to selectively develop desired portions of the displayed image.

* * * * *